US008349756B2

United States Patent
Lin et al.

(10) Patent No.: US 8,349,756 B2
(45) Date of Patent: Jan. 8, 2013

(54) NOBLE METAL-CONTAINING TITANOSILICATE MATERIAL AND ITS PREPARATION METHOD

(75) Inventors: Min Lin, Beijing (CN); Chunfeng Shi, Beijing (CN); Jun Long, Beijing (CN); Bin Zhu, Beijing (CN); Xingtian Shu, Beijing (CN); Xuhong Mu, Beijing (CN); Yibin Luo, Beijing (CN); Xieqing Wang, Beijing (CN); Yingchun Ru, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 456 days.

(21) Appl. No.: 12/594,008

(22) PCT Filed: Mar. 27, 2008

(86) PCT No.: PCT/CN2008/000616
§ 371 (c)(1),
(2), (4) Date: Sep. 30, 2009

(87) PCT Pub. No.: WO2008/119252
PCT Pub. Date: Oct. 9, 2008

(65) Prior Publication Data
US 2010/0105542 A1    Apr. 29, 2010

(51) Int. Cl.
*B01J 29/89* (2006.01)
(52) U.S. Cl. .................. 502/74; 502/77; 502/242
(58) Field of Classification Search .............. 502/74, 502/77, 242
See application file for complete search history.

(56) References Cited

U.S. PATENT DOCUMENTS

| 5,525,323 A | 6/1996 | Mueller et al. |
| 6,194,591 B1 | 2/2001 | Grey et al. |
| 6,867,312 B1 | 3/2005 | Jubin, Jr. et al. |

(Continued)

FOREIGN PATENT DOCUMENTS

CN         1301599 A    7/2001

(Continued)

OTHER PUBLICATIONS

Meiers, R. et al., "Synthesis of Propylene Oxide from Propylene, Oxygen, and Hydrogen Catalyzed by Palladium-Platinum-Containing Titanium Silicalite" *Journal of Catalysis* (1998) pp. 376-386, vol. 176.

(Continued)

*Primary Examiner* — David M Brunsman
(74) *Attorney, Agent, or Firm* — Scully, Scott, Murphy & Presser, P.C.

(57) ABSTRACT

A noble metal-containing titanosilicate material, characterized in that said material is represented with the oxide form of $xTiO_2 \cdot 100SiO_2 \cdot yEO_m \cdot zE$, wherein x ranges from 0.001 to 50.0; (y+z) ranges from 0.0001 to 20.0 and y/z<5; E represents one or more noble metals selected from the group consisting of Ru, Rh, Pd, Re, Os, Ir, Pt, Ag and Au; m is a number satisfying the oxidation state of E. The crystal grains of said material contain a hollow structure, or a sagging structure. In said material, the synergistic effect between the noble metal and the titanosilicate are enhanced. As compared with the prior art, the selectivity, catalytic activity and stability of the reaction product are obviously increased in the oxidation reaction, e.g. the reaction for preparing propylene oxide by epoxidation of propylene.

38 Claims, 9 Drawing Sheets

U.S. PATENT DOCUMENTS

| | | | |
|---|---|---|---|
| 6,884,898 B1 | 4/2005 | Miller | |
| 8,222,173 B2 * | 7/2012 | Yamashita et al. | 502/5 |
| 2005/0187394 A1 | 8/2005 | Dessau | |
| 2007/0112208 A1 | 5/2007 | Le-Khac et al. | |

FOREIGN PATENT DOCUMENTS

| | | |
|---|---|---|
| CN | 1358570 A | 7/2002 |
| CN | 1913968 A | 2/2007 |
| EP | 0634361 A1 | 1/1995 |
| EP | 0906784 A2 | 4/1999 |
| EP | 1 382 391 A1 | 1/2004 |
| JP | 03-044836 | 2/1991 |
| JP | 4-352771 A | 12/1992 |
| RU | 2243217 C2 | 12/2004 |
| RU | 2282587 C1 | 8/2006 |
| WO | WO94/19277 A1 | 9/1994 |
| WO | WO00/59632 A1 | 10/2000 |
| WO | WO01/83467 A1 | 11/2001 |
| WO | WO03/048143 A1 | 6/2003 |
| WO | WO2005/082533 A1 | 9/2005 |

OTHER PUBLICATIONS

Extended European Search Report dated Mar. 17, 2010 issued in EP08733849.

International Search Report dated Jun. 19, 2008 issued in PCT/CN2008/000616.

* cited by examiner

NOBLE METAL-CONTAINING TITANOSILICATE MATERIAL AND ITS PREPARATION METHOD

This application is a 371 filing of PCT/CN08/00616 filed Mar. 27, 2008.

TECHNICAL FIELD

The present invention relates to a titanosilicate material and its preparation method. Specifically, the present invention concerns a noble metal-containing titanosilicate material and its preparation method.

BACKGROUND OF THE INVENTION

Titanosilicate is a novel heteroatom molecular sieve developed from the early 1980s. The synthesized titanosilicate molecular sieves currently include TS-1 having the MFI-type structure, TS-2 having the MEL-type structure, Ti-MCM-22 having the MWW-type structure and TS-48 having a relatively greater pore structure. Among said titanosilicate molecular sieves, the titanosilicate TS-1 developed by Enichem, Italy, is a novel titanosilicate having excellent catalytic selectivity and oxidation property and formed by introducing a transition metal, titanium, into the molecular sieve framework having a ZSM-5 structure. TS-1 has not only the catalytic oxidation of titanium, but also the shape-selective function and excellent stability of ZSM-5 molecular sieves. The titanosilicate material as a catalyst can be used to catalyze various organic oxidations, such as epoxidation of olefins, partial oxidation of alkanes, oxidation of alcohols, hydroxylation of phenols, ammoxidation of cyclones and the like. In the oxidation of organic substances using TS-1 molecular sieves, hydrogen peroxide which is pollution free and in a low concentration may be used as an oxidizing agent, so as to avoid the complex technology and environmental pollution in the oxidation process. It also has the advantages of energy conservation, economization, environmental benign incomparable by the conventional oxidation system, and has better reaction selectivity. Thus it has a great industrial application prospect. The titanosilicate as a catalyst for selective oxidation of organic substances is deemed to a milestone in the field of molecular sieve catalysis.

$H_2O_2$ is a well-acknowledged green oxidizing agent, and the by-product of oxidation merely includes water. However, the aqueous solution of $H_2O_2$ is difficult to be stored and transported. $H_2O_2$ is extremely unstable and will be decomposed when being in contact with heat, light, rough surface, heavy metals and other impurities. Moreover, special safety measures shall be taken during the packaging, storage and transportation due to the corrosivity thereof. Thus such chemical product can be effectively used only if $H_2O_2$ is used on-site, or the production process of $H_2O_2$ is combined with the downstream process in which $H_2O_2$ is used.

$H_2O_2$ can be directly synthesized by using $H_2$ and $O_2$, and the atom utilization rate reaches 100%. Thus people hope to use $H_2$ and $O_2$ to in situ synthesize $H_2O_2$ and then oxidize the organic material, so as to solve the cost and safety problems induced by directly using $H_2O_2$. Since Pt, Pd, Au and so on are the effective components for synthesizing $H_2O_2$ by using $H_2$ and $O_2$, many patent documents reported the studies on supporting them on the titanosilicate material to in situ produce $H_2O_2$ for the selective oxidation of organic substances. For example, Meiers R. et al (J. Catal., 1998, 176:376-386) made studies on the propylene gas phase epoxidation by using Pt—Pd/TS-1 as the catalyst. In addition, U.S. Pat. No. 6,867,312B1 and U.S. Pat. No. 6,884,898B1 also made such studies. Although said technique is carried out under mild reaction conditions and has a good selectivity (may higher than 95%), there are the shortages of relatively lower catalyst activity, worse catalyst stability and the like. Thus the key points of the research and development of said technique lie in preparing and modifying the corresponding catalysts so as to enhance the conversion rate of the reactions, and improving the anti-inactivation and regenerability of the catalyst.

DESCRIPTION OF THE INVENTION

In view of the shortages that the noble metals such as Pt, Pd, Au and the like are supported on the titanosilicate material to in situ produce $H_2O_2$ for the selective oxidizing reaction process of organic substances, the present invention provides a noble metal-containing titanosilicate material and its preparation method.

The noble metal-containing titanosilicate material provided in the present invention is characterized in that said material is represented with the oxide form of $xTiO_2 \cdot 100SiO_2 \cdot yEO_m \cdot zE$, wherein x ranges from 0.001 to 50.0; (y+z) ranges from 0.0001 to 20.0 and y/z<5; E represents one or more noble metals selected from the group consisting of Ru, Rh, Pd, Re, Os, Ir, Pt, Ag and Au; m is a number satisfying the oxidation state of E. The crystal grains of said material contain a hollow structure, or a sagging (concavo-convex) structure.

In the noble metal-containing titanosilicate material provided in the present invention, x ranges preferably from 0.005 to 25 or from 0.001 to 20, more preferably from 0.005 to 20; (y+z) ranges preferably from 0.005 to 20 or from 0.001 to 10, more preferably from 0.005 to 10, most preferably from 0.01 to 7; y/z is preferably less than 3, more preferably less than 2, more preferably less than 1, most preferably from 0.01 to 0.8. Said noble metal is preferably one or more selected from the group consisting of Pd, Pt, Ag and Au, more preferably Pd and/or Pt. When the noble metal are two or more selected from the group, said y value is the sum of y value of each noble metal; and said z value is the sum of z value of each noble metal. For example, when the noble metal are Pt and Pd, said material is represented with the oxide form of $xTiO_2 \cdot 100SiO_2 \cdot y_1PtO \cdot y_2PdO \cdot z_1Pt \cdot z_2Pd$, i.e. $y=y_1+y_2$; and $z=z_1+z_2$. The crystal grains of said material fully or partially contain a hollow structure, and the cavity portion of the hollow crystal grains of said material has a radial length of 0.1-500 nm, preferably 0.5-300 nm. The benzene adsorption capacity of said material is at least 25 mg/g, preferably at least 35 mg/g, measured under the conditions of a temperature of 25° C., $P/P_0=0.10$ and the adsorption time of 1 h. There is a hysteresis loop between the adsorption isotherm and desorption isotherm of the low-temperature nitrogen adsorption of said material. At a relative pressure $P/P_0$ of about 0.60, the difference between the nitrogen adsorption capacity during the desorption and the nitrogen adsorption capacity during the adsorption is greater than 2% of the nitrogen adsorption capacity during the adsorption. The cavity portion shape thereof can be varied, not a fixed shape, such as in circular, or rectangular, or irregularly polygonal, or irregularly circular, or combinations of these shapes. The crystal grains of said material are single crystal grains or are aggregate crystal grains aggregated from a plurality of crystal grains.

The crystal grains of the material provide in the present invention may fully or partially contain a hollow or a sagging structure.

As for the material provided in the present invention, the hollow crystal grains are advantageous to the dispersion of the reactants and the product molecules, so as to enhance the synergistic effect between the noble metal and the titanosilicate; and noble metals have better dispersibility. Moreover, the hollow structure of the noble metal-containing titanosilicate material provided in the present invention has a strong capability of accommodating carbon deposit. As compared with the prior art (e.g. the conventional impregnation support technique), the selectivity, catalytic activity and stability of the reaction product are obviously increased in the oxidation reaction, e.g. the reaction for preparing propylene oxide by epoxidation of propylene.

The present invention further provides two methods for preparing the noble metal-containing titanosilicate material above.

One of the methods provided in the present invention comprises homogeneously mixing titanosilicate, protecting agent, noble metal source, reducing agent, alkali source with water, feeding the mixture into a reaction kettle for hydrothermal treatment, filtering, washing, drying to obtain the material. More specifically, said method comprises the steps of (1) homogeneously mixing titanosilicate, protecting agent, noble metal source, reducing agent, alkali source with water to obtain a mixture having a titanosilicate (g):protecting agent (molar):alkali source (molar):reducing agent (molar):noble metal source (g, calculated with single substance of noble metal):water (molar) ratio of 100:(0.0-5.0):(0.005-5.0):(0.005-15.0):(0.005-10.0):(200-10000); and (2) feeding the mixture obtained in step (1) into the reaction kettle, reacting under the hydrothermal treatment conditions, recovering the product to obtain a titanosilicate material.

In said first preparation method, the mixture has a preferred titanosilicate (g):protecting agent (molar):alkali source (molar):reducing agent (molar):noble metal source (g, calculated with single substance of noble metal):water molar ratio of 100:(0.005-1.0):(0.01-2.0):(0.01-10.0):(0.01-5.0):(500-5000).

In the first preparation method above, the titanosilicate in step (1) includes various types of titanosilicate molecular sieves having various structures, e.g. TS-1, TS-2, Ti-BETA, Ti-MCM-22, Ti-MCM-41, Ti-ZSM-48, Ti-ZSM-12, Ti-MMM-1, Ti-SBA-15, Ti-MSU, Ti-MCM-48, and the like, preferably TS-1.

In the first preparation method above, the protecting agent is a polymer or surfactant, wherein the polymer is selected from the group consisting of polypropylene, polyethyleneglycol, polystyrene, polyvinyl chloride, polyethylene and derivatives thereof; and the surfactant is selected from the group consisting of anionic surfactant, cationic surfactant and nonionic surfactant.

The reducing agent in step (1) of the aforesaid preparation method may be selected from the group consisting of hydrazine, borohydride and sodium citrate, wherein the hydrazine is selected from the group consisting of hydrazine hydrate, hydrazine hydrochloride and hydrazine sulphate; and said borohydride is selected from the group consisting of sodium borohydride and potassium borohydride.

The noble metal source in step (1) of the aforesaid preparation method is an inorganic or organic substance of said noble metal, which may be selected from the group consisting of oxides, halides, carbonates, nitrates, ammonium nitrates, sal ammoniac salts, hydroxides, and other complexes of the noble metal. Taking palladium as an example, the palladium source may be an inorganic and/or organic palladium source, wherein the inorganic palladium source is selected from the group consisting of palladium oxide, palladium carbonate, palladium chloride, palladium nitrate, palladium ammonium nitrate, palladium sal ammoniac, palladium hydroxide and other complexes of palladium; the organic palladium source is selected from the group consisting of palladium acetate and palladium acetylacetone.

The alkali source in step (1) of the aforesaid preparation method is an inorganic or organic alkali source, wherein the inorganic alkali source is selected from the group consisting of ammonia, sodium hydroxide, potassium hydroxide and barium hydroxide; and the organic alkali source is selected from the group consisting of carbamide, quaternary ammonium alkali compounds, aliphatic amine compounds, alcohol amine compounds, and mixtures thereof.

The quaternary ammonium alkali compounds have a general formula of $(R^1)_4NOH$, wherein $R^1$ is alkyl having 1-4 carbon atoms, preferably propyl.

The aliphatic amine compounds have a general formula of $R^2(NH_2)_n$, wherein $R^2$ is alkyl or alkylidene having 1-6 carbon atoms, and n is 1 or 2. The aliphatic amine compounds are selected from the group consisting of ethylamine, n-butylamine, butanediamine and hexanediamine.

The alcohol amine compounds have a general formula of $(HOR^3)_mNH_{(3-m)}$, wherein $R^3$ is alkyl having 1-4 carbon atoms, and m is 1, 2 or 3. The alcohol amine compounds are selected from the group consisting of monoethanolamine, diethanolamine and triethanolamine In the first preparation method above, a protecting agent may or may not be added.

The hydrothermal treatment conditions in step (2) of the aforesaid preparation method refer to the hydrothermal treatment for 2-360 h at a temperature of 80-200° C. and an autogenous pressure. Said recovering process is well known by those skilled in the art, and there is nothing special about it. Said recovering process generally comprises the processes, such as washing, drying of the crystallized product, and the like.

The second preparation method provided in the present invention specifically comprises the steps of (1) homogeneously mixing titanium source, silicon source, alkali source, protecting agent, noble metal source with water to obtain a mixture having a silicon source:titanium source:alkali source:noble metal source:protecting agent:water molar ratio of 100:(0.005-50.0):(0.005-20.0):(0.005-10.0):(0.0001-5.0):(200-10000), wherein the silicon source is calculated with $SiO_2$; the titanium source is calculated with $TiO_2$; and the noble metal source is calculated with simple substance; hydrothermally crystallizing the mixture for at least 2 hrs at 120-200° C., taking out, filtering, drying and calcining the product to obtain an intermediate crystalline material; and (2) feeding the intermediate crystalline material obtained in step (1) into the remnant filtrate in step (1), adding a reducing agent in a molar ratio of 0.1-10 to the noble metal source added in step (1), hydrothermally treating for 2-360 h at 80-200° C. and an autogenous pressure, and recovering the product to obtain the titanosilicate material of the present invention.

In the second preparation method provided in the present invention, step (2) may be repeated once or many times if necessary.

In the second preparation method provided in the present invention, the mixture in step (1) has a preferred silicon source:titanium source:alkali source:noble metal source:protecting agent:water molar ratio of 100:(0.01-10.0):(0.01-10.0):(0.01-5.0):(0.0005-1.0):(500-5000).

In the second preparation method provided in the present invention, the silicon source in step (1) is selected from the group consisting of silica gel, silica sol and organic silicate, preferably organic silicate. The organic silicate has the general formula $R^4{}_4SiO_4$, wherein $R^4$ is alkyl having 1-4 carbon atoms, preferably ethyl.

In the second preparation method provided in the present invention, the titanium source is an inorganic titanium salt or an organic titanate, preferably organic titanate. The inorganic titanium salt is selected from the group consisting of $TiCl_4$, $Ti(SO_4)_2$ and $TiOCl_2$. The organic titanate has the general formula of $Ti(OR^5)_4$, wherein $R^5$ is alkyl having 1-6 carbon atoms, preferably alkyl having 2-4 carbon atoms.

In the second preparation method provided in the present invention, the alkali source in step (1) is a quaternary ammonium alkali compound or a mixture of a quaternary ammonium alkali compound, an aliphatic amine compound and an alcohol amine compound. The quaternary ammonium alkali compound has the general formula of $(R^6)_4NOH$, wherein $R^6$ is alkyl having 1-4 carbon atoms, preferably propyl. The aliphatic amine compound has the general formula of $R^7(NH_2)_n$, wherein $R^7$ is alkyl or alkylidene having 1-6 carbon atoms, and n is 1 or 2. The aliphatic amine compound is selected from the group consisting of ethylamine, n-butylamine, butanediamine and hexanediamine. The alcohol amine compound has the general formula of $(HOR^8)_mNH_{(3-m)}$, wherein $R^8$ is alkyl having 1-4 carbon atoms, and m is 1, 2 or 3. The alcohol amine compound is selected from the group consisting of monoethanolamine, diethanolamine and triethanolamine In the second preparation method provided in the present invention, the protecting agent is a polymer or surfactant, wherein the polymer is selected from the group consisting of polypropylene, polyethyleneglycol, polystyrene, polyvinyl chloride, polyethylene and derivatives thereof; and the surfactant is selected from the group consisting of anionic surfactant, cationic surfactant and nonionic surfactant.

The noble metal source in step (1) of the aforesaid second preparation method is an inorganic or organic substance of said noble metal, which may be selected from the group consisting of oxides, halides, carbonates, nitrates, ammonium nitrates, sal ammoniac salts, hydroxides, and other complexes of the noble metal. Taking palladium as an example, the palladium source may be an inorganic and/or organic palladium source, wherein the inorganic palladium source is selected from the group consisting of palladium oxide, palladium carbonate, palladium chloride, palladium nitrate, palladium ammonium nitrate, palladium sal ammoniac, palladium hydroxide and other complexes of palladium; the organic palladium source is selected from the group consisting of palladium acetate and palladium acetylacetone.

In the second preparation method provided in the present invention, the reducing agent in step (1) is selected from the group consisting of hydroxylamine, hydrazine, borohydride and sodium citrate, wherein the hydrazine is selected from the group consisting of hydrazine hydrate, hydrazine hydrochloride and hydrazine sulphate; and said borohydride is selected from the group consisting of sodium borohydride and potassium borohydride.

As compared with the prior art, the catalytic and oxidizing activity and the product selectivity of the preparation methods provided in the present invention are obviously increased. Meanwhile, said methods have better catalytic activity and stability (see Example 12). In addition, since the hollow or sagging structure contained by the crystal grains of the material provided in the present application is advantageous to the dispersion of the reactants and the product molecule, especially macromolecules (e.g. aromatic compounds), in the catalytic reaction, it is specially advantageous to the catalytic oxidation of aromatic compounds, cycle compounds and the like.

MODE OF CARRYING OUT THE INVENTION

The following examples make further explanations to the present invention, but do not hereby limit the present invention.

The reagents used in the examples all were the commercial products of chemically pure reagents. The titanosilicate TS-1 used in the comparative examples and examples was prepared according to the method as described in the prior art of Zeolites, 1992, Vol. 12, 943; the titanosilicate Ti-BETA used therein was prepared according to the method as described in the prior art of J. Catal., 1994, Vol. 145, 151; the titanosilicate TS-2 used in the comparative examples and examples was prepared according to the method as described in the prior art of Appl. Catal., 1990, Vol. 58, L1; the titanosilicate Ti-ZSM-48 used therein was prepared according to the method as described in the prior art of J. Chem. Soc. Chem. Commun., 1994, 745; and the titanosilicate Ti-ZSM-12 used therein was prepared according to the method as described in the prior art of Zeolites, 1995, Vol. 15, 236. The adsorption-desorption isothermal curve of the low-temperature nitrogen adsorption of the samples are determined according to the ASTM D4222-98 standard method on ASAP2405 Static Nitrogen Adsorption Device of Micromeritics, USA. The Transmission Electron Microscope (TEM) photographs of the samples were obtained via the Tecnai G2F20S-TWIN-type transmission electron microscope of FEI, Holland, wherein the accelerating voltage was 20 kV. In addition, the benzene adsorption amount of the samples was determined by the conventional static adsorption process.

COMPARATIVE EXAMPLE 1

This comparative example shows the process of the conventional preparation of the supported-type palladium/titanosilicate catalyst.

Figure 1:
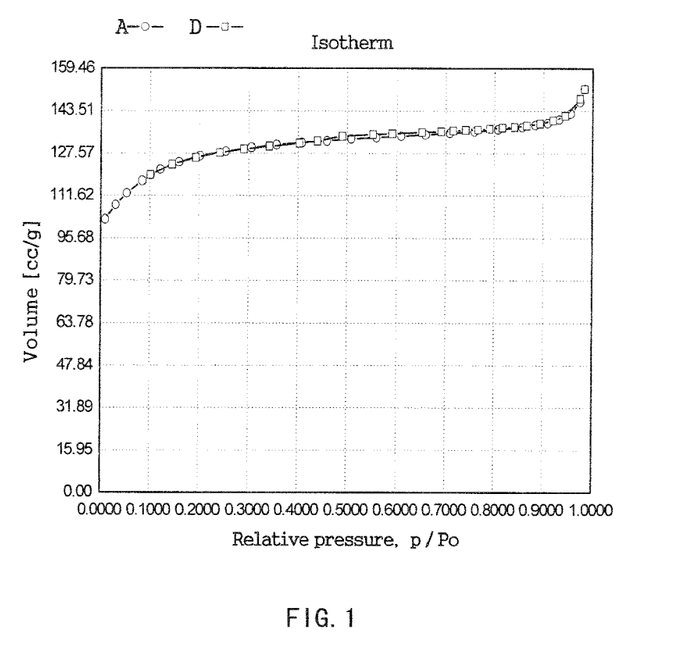
FIG. 1 shows the adsorption-desorption isothermal curve of the low-temperature nitrogen adsorption of Comparative sample DB-1 in Comparative Example 1.
Figure 13:
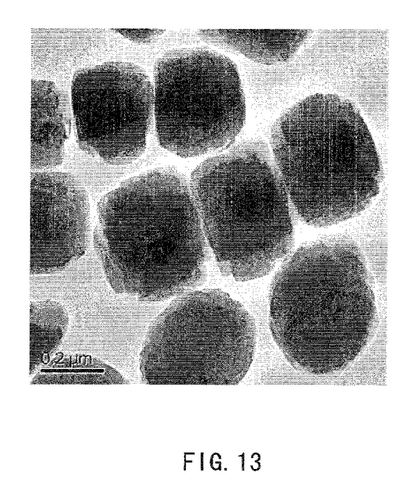
FIG. 13 shows the Transmission Electron Microscope (TEM) photograph of Comparative Example DB-1 in Comparative example 1.

20 g of the titanosilicate TS-1 and 20 ml palladium ammonium nitrate complex solution having a concentration of 0.01 g/ml (calculated with palladium atom) were added to 20 ml of deionized water. The mixture was homogeneously stirred, properly sealed, impregnated for 24 h at a temperature of 40° C., naturally dried and reduction-activated for 3 h in a hydrogen atmosphere at 150° C. to obtain the conventional supported-type palladium/titanosilicate catalyst DB-1. Upon characterization, the catalyst was represented with the oxide form of $6TiO_2.100SiO_2.0.7PdO.0.3Pd$. There was no hysteresis loop in the adsorption-desorption isothermal curve of the low-temperature nitrogen adsorption (FIG. 1). The Transmission Electron Microscope (TEM) photograph showed a solid structure, rather than a hollow or a sagging structure (FIG. 13).

EXAMPLE 1

Figure 2:
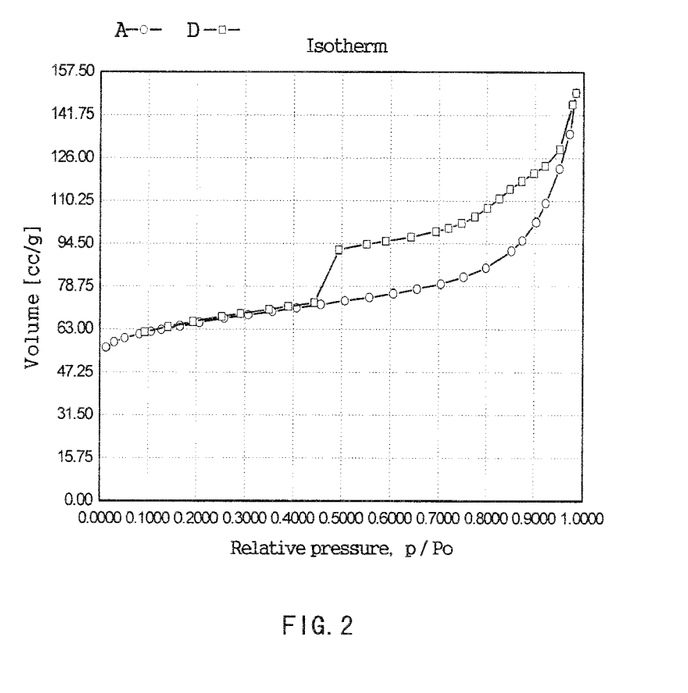
FIG. 2 shows the adsorption-desorption isothermal curve of the low-temperature nitrogen adsorption of Sample A in Example 1.
Figure 14:
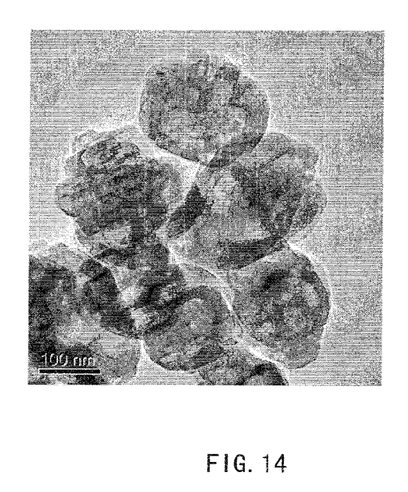
FIG. 14 shows the Transmission Electron Microscope (TEM) photograph of Sample A in Example 1.

20 g of the titanosilicate TS-1, palladium ammonium nitrate complex solution having a concentration of 0.01 g/ml (calculated with palladium atom), a suitable amount of hydrazine hydrate and cetyl trimethyl ammonium bromide were added to an aqueous solution of tetrapropylammonium hydroxide (having a mass percent concentration of 10%), homogeneously mixed and stirred to obtain a mixture having a titanosilicate (g):cetyl trimethyl ammonium bromide (molar):tetrapropylammonium hydroxide (molar):hydrazine hydrate (molar):palladium ammonium nitrate complex (g, calculated with palladium):water (molar) ratio of 100:0.005:0.5:3.0:2.0:1000. The mixture was then fed into the stainless steel sealed reaction kettle, hydrothermally treated for 48 h at 150° C. and an autogenous pressure. The resulted substance was filtered, washed with water, naturally dried, and further dried at 180° C. for 3 h to obtain the novel noble metal-containing titanosilicate material A of the present invention. Upon characterization, the material was represented with the oxide form of $4TiO_2.100SiO_2.0.01PdO.0.09Pd$. There was a hysteresis loop in the adsorption-desorption isothermal curve of the low-temperature nitrogen adsorption (FIG. 2). The Transmission Electron Microscope (TEM) photograph showed a hollow structure (FIG. 14).

EXAMPLE 2

Figure 3:
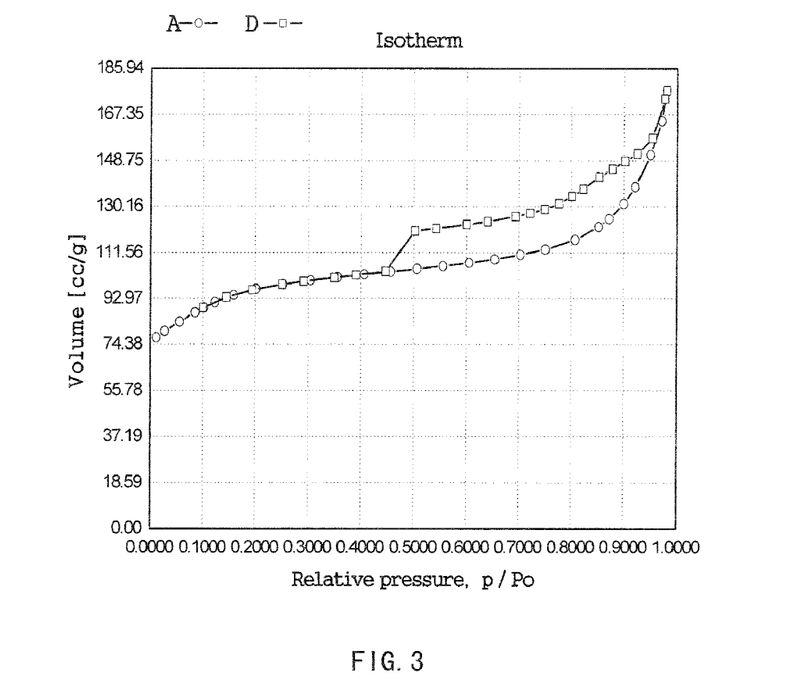
FIG. 3 shows the adsorption-desorption isothermal curve of the low-temperature nitrogen adsorption of Sample B in Example 2.
Figure 15:
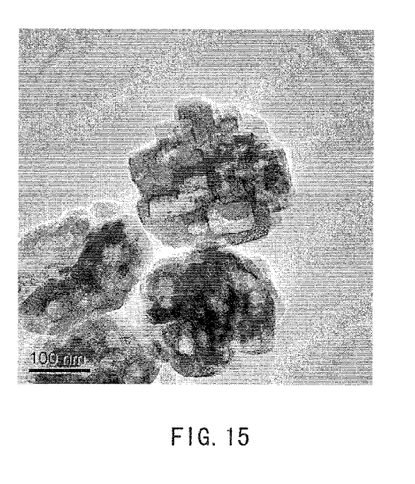
FIG. 15 shows the Transmission Electron Microscope (TEM) photograph of Sample B in Example 2.

20 g of the titanosilicate Ti-BETA, palladium chloride complex solution having a concentration of 0.01 g/ml (calculated with palladium atom), a suitable amount of hydrazine hydrochloride and polypropylene were added to an aqueous solution of sodium hydroxide (having a mass percent concentration of 15%), homogeneously mixed and stirred to obtain a mixture having a titanosilicate (g):polypropylene (molar):sodium hydroxide (molar):hydrazine hydrochloride (molar):palladium chloride (g, calculated with palladium):water (molar) ratio of 100:0.9:1.8:0.15:0.1:4600. The mixture was then fed into the stainless steel sealed reaction kettle, hydrothermally treated for 24 h at 180° C. and an autogenous pressure. The resulted substance was filtered, washed with water, naturally dried, and further dried at 110° C. for 3 h to obtain the novel noble metal-containing titanosilicate material B of the present invention. Upon characterization, the material was represented with the oxide form of $8TiO_2.100SiO_2.0.006PdO.0.008Pd$. There was a hysteresis loop in the adsorption-desorption isothermal curve of the low-temperature nitrogen adsorption (FIG. 3). The Transmission Electron Microscope (TEM) photograph showed a hollow structure (FIG. 15).

EXAMPLE 3

Figure 4:
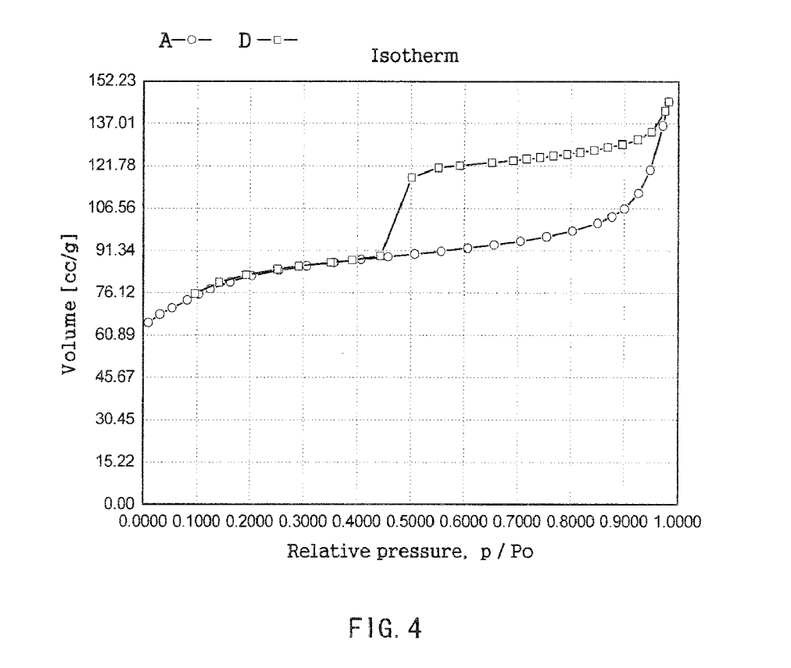
FIG. 4 shows the adsorption-desorption isothermal curve of the low-temperature nitrogen adsorption of Sample C in Example 3.
Figure 16:
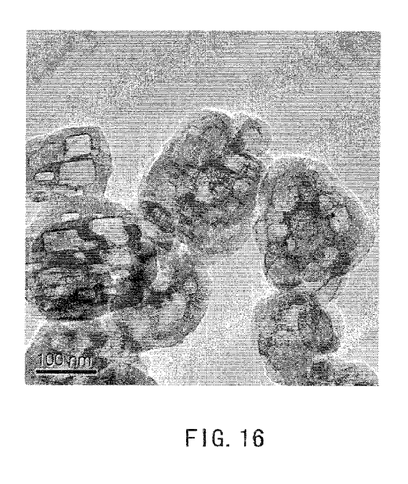
FIG. 16 shows the Transmission Electron Microscope (TEM) photograph of Sample C in Example 3.

Tetraethyl orthosilicate, tetrabutyl titanate, palladium acetate having a concentration of 0.01 g/ml (calculated with palladium atom) and Tween 80 were added to an aqueous solution of tetrapropyl ammonium hydroxide and butanediamine (having a mass percent concentration of 10%), homogeneously mixed and stirred to obtain a mixture having a silicon source:titanium source:alkali source:palladium source:protecting agent:water ratio of 100:0.03:0.5:0.05:0.02:550, wherein the silicon source is calculated with $SiO_2$ the titanium source is calculated with $TiO_2$; the palladium source is calculated with Pd. The mixture was then fed into the sealed reaction kettle, hydrothermally treated for 120 h at 120° C. and an autogenous pressure. The resulted substance was taken out, filtered, dried, and calcined to obtain the intermediate crystalline material. Said intermediate crystalline material was fed into the remnant filtrate, and then a suitable amount of hydrazine hydrate was then added for hydrothermal treatment for 36 h at 170° C. and an autogenous pressure. The resulted substance was filtered, washed with water, naturally dried and further dried for 3 h at 150° C. to obtain the novel noble metal-containing titanosilicate material C of the present invention. Upon characterization, the material was represented with the oxide form of $0.008TiO_2.100SiO_2.0.01PdO.0.2Pd$. There was a hysteresis loop in the adsorption-desorption isothermal curve of the low-temperature nitrogen adsorption (FIG. 4). The Transmission Electron Microscope (TEM) photograph showed a hollow structure (FIG. 16).

EXAMPLE 4

Figure 5:
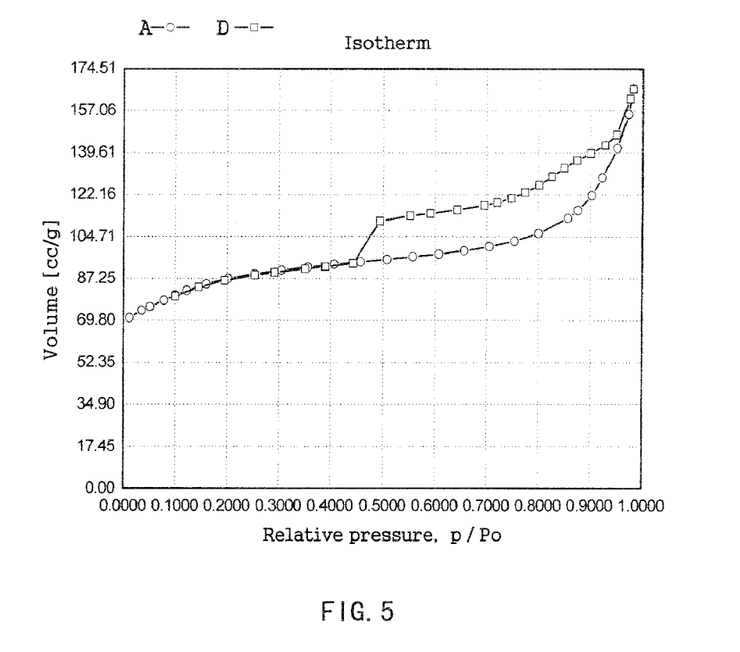
FIG. 5 shows the adsorption-desorption isothermal curve of the low-temperature nitrogen adsorption of Sample D in Example 4.
Figure 17:
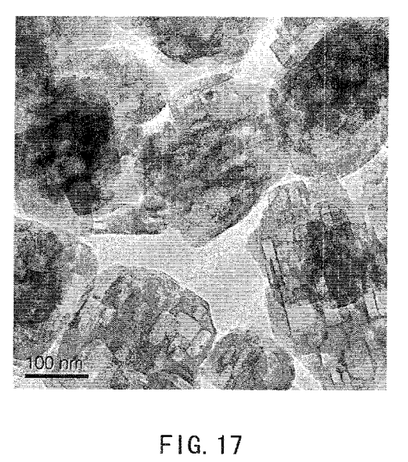
FIG. 17 shows the Transmission Electron Microscope (TEM) photograph of Sample D in Example 4.

Silica sol, tetrabutyl titanate, palladium sal ammoniac having a concentration of 0.01 g/ml (calculated with palladium atom) and sodium dodecyl benzene sulfonate were added to an aqueous solution of tetrapropyl ammonium hydroxide and butanediamine (having a mass percent concentration of 15%), homogeneously mixed and stirred to obtain a mixture having a silicon source:titanium source:alkali source:palladium source:protecting agent:water ratio of 100:2.0:5.2:2.0:0.5:2500, wherein the silicon source is calculated with $SiO_2$ the titanium source is calculated with $TiO_2$; the palladium source is calculated with Pd. The mixture was then fed into the stainless steel sealed reaction kettle, hydrothermally treated for 96 h at 150° C. and an autogenous pressure. The resulted substance was taken out, filtered, dried, and calcined to obtain the intermediate crystalline material. Said intermediate crystalline material was fed into the remnant filtrate, and then a suitable amount of hydrazine hydrochloride was then added for hydrothermal treatment for 48 h at 120° C. and an autogenous pressure. The resulted substance was filtered, washed with water, naturally dried and further dried for 3 h at 120° C. to obtain the novel noble metal-containing titanosilicate material D of the present invention. Upon characterization, the material was represented with the oxide form of $19TiO_2.100SiO_2.0.5PdO.1.3Pd$. There was a hysteresis loop in the adsorption-desorption isothermal curve of the low-temperature nitrogen adsorption (FIG. 5). The Transmission Electron Microscope (TEM) photograph showed a hollow structure (FIG. 17).

EXAMPLE 5

Figure 6:
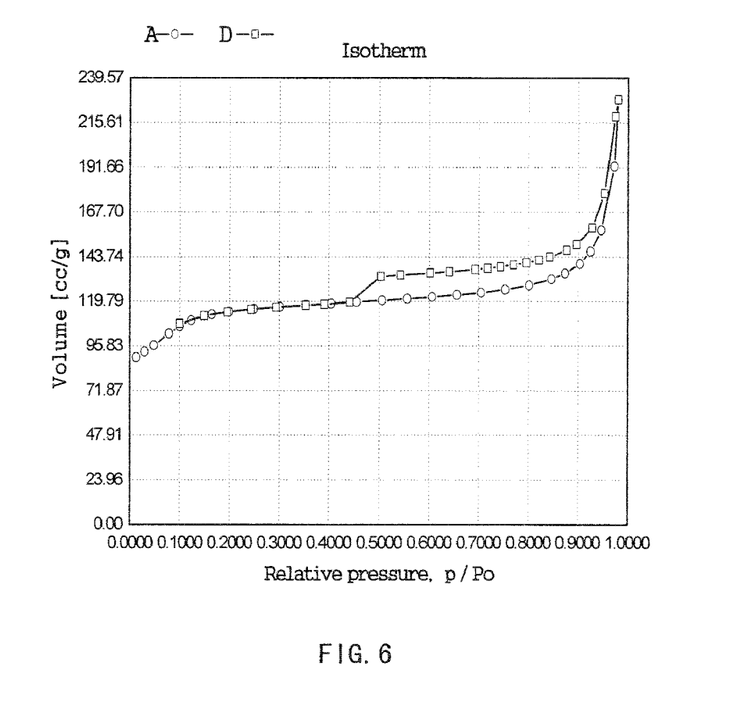
FIG. 6 shows the adsorption-desorption isothermal curve of the low-temperature nitrogen adsorption of Sample E in Example 5.
Figure 18:
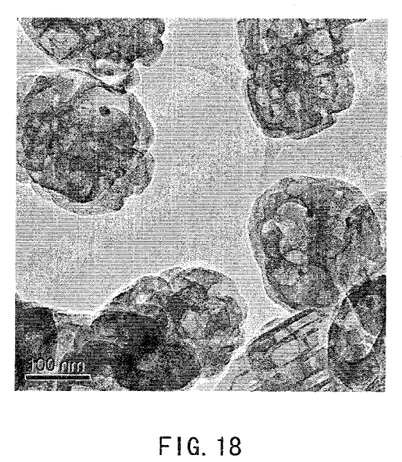
FIG. 18 shows the Transmission Electron Microscope (TEM) photograph of Sample E in Example 5.

20 g of the titanosilicate TS-2, palladium acetate having a concentration of 0.01 g/ml (calculated with palladium atom), a suitable amount of sodium borohydride and Tween 80 were added to an aqueous solution of butanediamine (having a mass percent concentration of 10%), homogeneously mixed and stirred to obtain a mixture having a titanosilicate (g):Tween 80 (molar):butanediamine (molar):sodium borohydride (molar):palladium acetate (g, calculated with palladium):water (molar) ratio of 100:0.1:0.02:0.05:0.03:520. The mixture was then fed into the stainless steel sealed reaction kettle, hydrothermally treated for 120 h at 120° C. and an autogenous pressure. The resulted substance was filtered, washed with water, naturally dried and further dried for 3 h at 150° C. to obtain the novel noble metal-containing titanosilicate material E of the present invention. Upon characterization, the material was represented with the oxide form of $0.1TiO_2.100SiO_2.0.66PdO.0.12Pd$. There was a hysteresis loop in the adsorption-desorption isothermal curve of the low-temperature nitrogen adsorption (FIG. 6). The Transmission Electron Microscope (TEM) photograph showed a hollow structure (FIG. 18).

EXAMPLE 6

Figure 7:
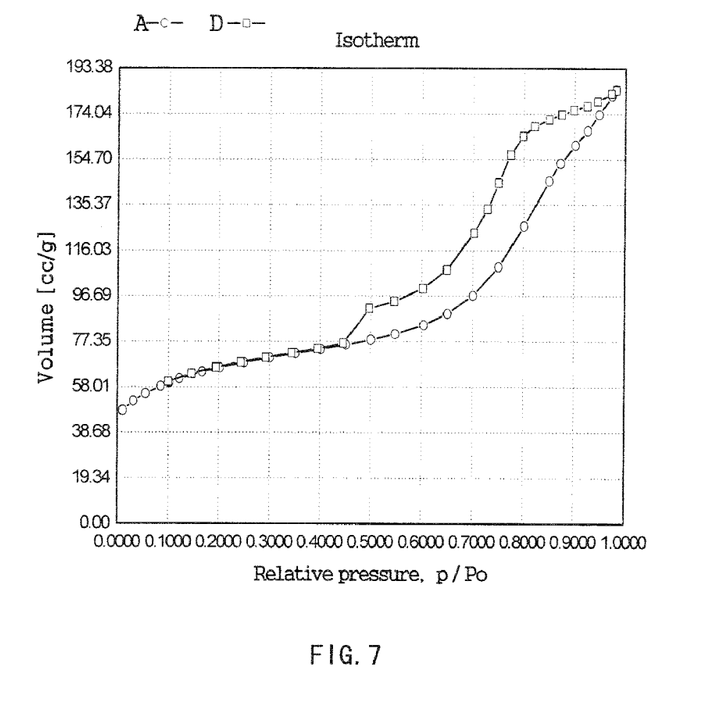
FIG. 7 shows the adsorption-desorption isothermal curve of the low-temperature nitrogen adsorption of Sample F in Example 6.
Figure 19:
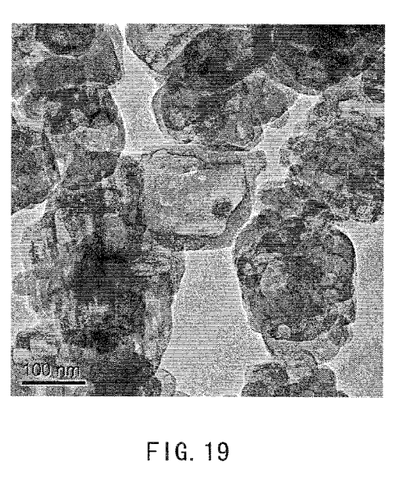
FIG. 19 shows the Transmission Electron Microscope (TEM) photograph of Sample F in Example 6.

20 g of the titanosilicate Ti-ZSM-48, palladium sal ammoniac having a concentration of 0.01 g/ml (calculated with palladium atom), a suitable amount of hydrazine sulphate and Pluronic P123 were added to an aqueous solution of tetrapropyl ammonium hydroxide (having a mass percent concentration of 10%), homogeneously mixed and stirred to obtain a mixture having a titanosilicate (g):Pluronic P123 (molar):tetrapropyl ammonium hydroxide (molar):hydrazine sulphate (molar):palladium sal ammoniac (g, calculated with palladium):water (molar) ratio of 100:0.5:0.1:8.5:4.8:2000. The mixture was then fed into the stainless steel sealed reaction kettle, hydrothermally treated for 240 h at 90° C. and an autogenous pressure. The resulted substance was filtered, washed with water, naturally dried and further dried for 3 h at 120° C. to obtain the novel noble metal-containing titanosilicate material F of the present invention. Upon characterization, the material was represented with the oxide form of $0.04TiO_2.100SiO_2.3.6PdO.1.1Pd$. There was a hysteresis loop in the adsorption-desorption isothermal curve of the low-temperature nitrogen adsorption (FIG. 7). The Transmission Electron Microscope (TEM) photograph showed a hollow structure (FIG. 19).

EXAMPLE 7

Figure 8:
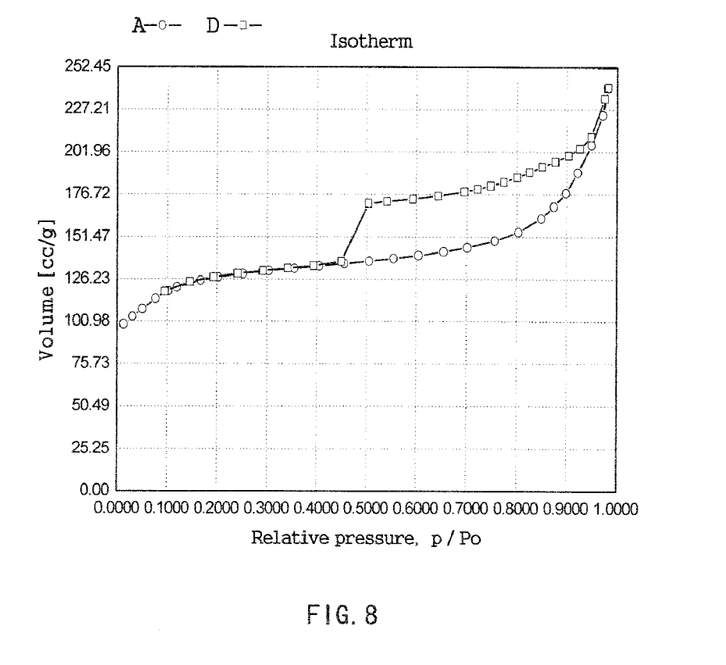
FIG. 8 shows the adsorption-desorption isothermal curve of the low-temperature nitrogen adsorption of Sample G in Example 7.
Figure 20:
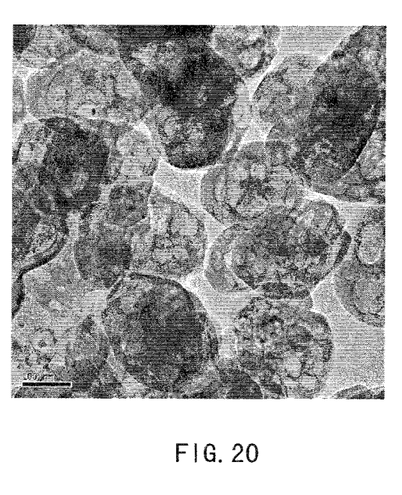
FIG. 20 shows the Transmission Electron Microscope (TEM) photograph of Sample G in Example 7.

Tetraethyl orthosilicate, tetraethyl titanate, palladium acetate having a concentration of 0.01 g/ml (calculated with palladium atom) and cetyl trimethyl ammonium bromide were added to an aqueous solution of tetrapropyl ammonium hydroxide (having a mass percent concentration of 13%), homogeneously mixed and stirred to obtain a mixture having a silicon source:titanium source:alkali source:palladium source:protecting agent:water ratio of 100:8.2:7.5:0.1:0.005:800, wherein the silicon source is calculated with $SiO_2$ the titanium source is calculated with $TiO_2$; the palladium source is calculated with Pd. The mixture was then fed into the sealed reaction kettle, hydrothermally treated for 96 h at 160° C. and an autogenous pressure. The resulted substance was taken out, filtered, dried, and calcined to obtain the intermediate crystalline material. Said intermediate crystalline material was fed into the remnant filtrate, and then a suitable amount of hydrazine hydrochloride was then added for hydrothermal treatment for 36 h at 170° C. and an autogenous pressure. The resulted substance was filtered, washed with water, naturally dried and further dried for 3 h at 150° C. to obtain the novel noble metal-containing titanosilicate material G of the present invention. Upon characterization, the material was represented with the oxide form of $23TiO_2.100SiO_2.0.004PdO.0.8Pd$. There was a hysteresis loop in the adsorption-desorption isothermal curve of the low-temperature nitrogen adsorption (FIG. 8). The Transmission Electron Microscope (TEM) photograph showed a hollow structure (FIG. 20).

EXAMPLE 8

Figure 9:
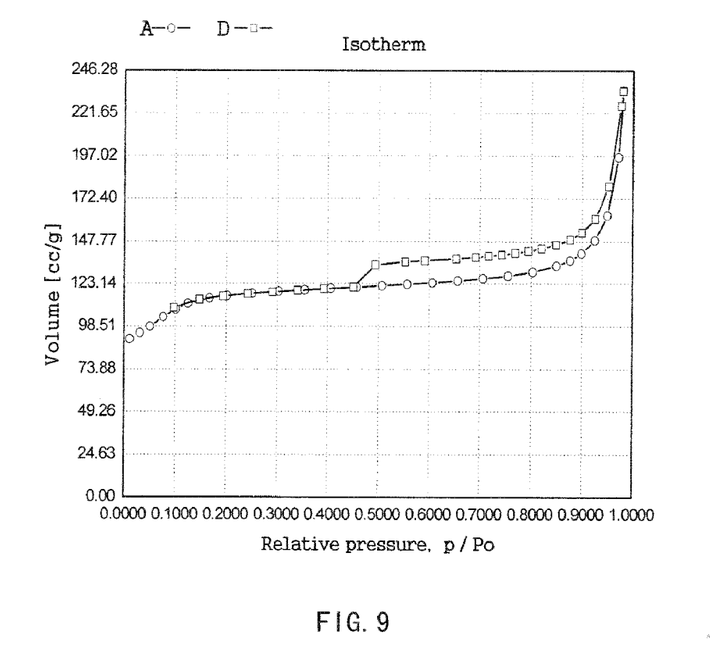
FIG. 9 shows the adsorption-desorption isothermal curve of the low-temperature nitrogen adsorption of Sample H in Example 8.
Figure 21:
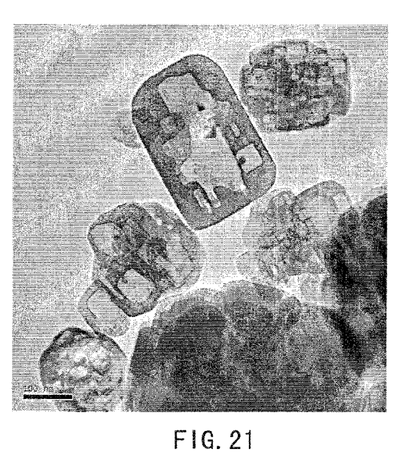
FIG. 21 shows the Transmission Electron Microscope (TEM) photograph of Sample H in Example 8.

Tetramethyl orthosilicate, $TiCl_4$, palladium ammonium nitrate having a concentration of 0.01 g/ml (calculated with palladium atom) and polychlorovinyl were added to an aqueous solution of tetrapropyl ammonium hydroxide (having a mass percent concentration of 15%), homogeneously mixed and stirred to obtain a mixture having a silicon source:titanium source:alkali source:palladium source:protecting agent:water ratio of 100:5.0:0.02:4.5:0.9:4800, wherein the silicon source is calculated with $SiO_2$, the titanium source is calculated with $TiO_2$; the palladium source is calculated with Pd. The mixture was then fed into the sealed reaction kettle, hydrothermally treated for 96 h at 150° C. and an autogenous pressure. The resulted substance was taken out, filtered, dried, and calcined to obtain the intermediate crystalline material. Said intermediate crystalline material was fed into the remnant filtrate, and then a suitable amount of sodium borohydride was then added for hydrothermal treatment for 48 h at 120° C. and an autogenous pressure. The resulted substance was filtered, washed with water, naturally dried and further dried for 3 h at 120° C. to obtain the novel noble metal-containing titanosilicate material H of the present invention. Upon characterization, the material was represented with the oxide form of $12TiO_2.100SiO_2.0.01PdO.6.4Pd$. There was a hysteresis loop in the adsorption-desorption isothermal curve of the low-temperature nitrogen adsorption (FIG. 9). The Transmission Electron Microscope (TEM) photograph showed a hollow structure (FIG. 21).

EXAMPLE 9

Figure 10:
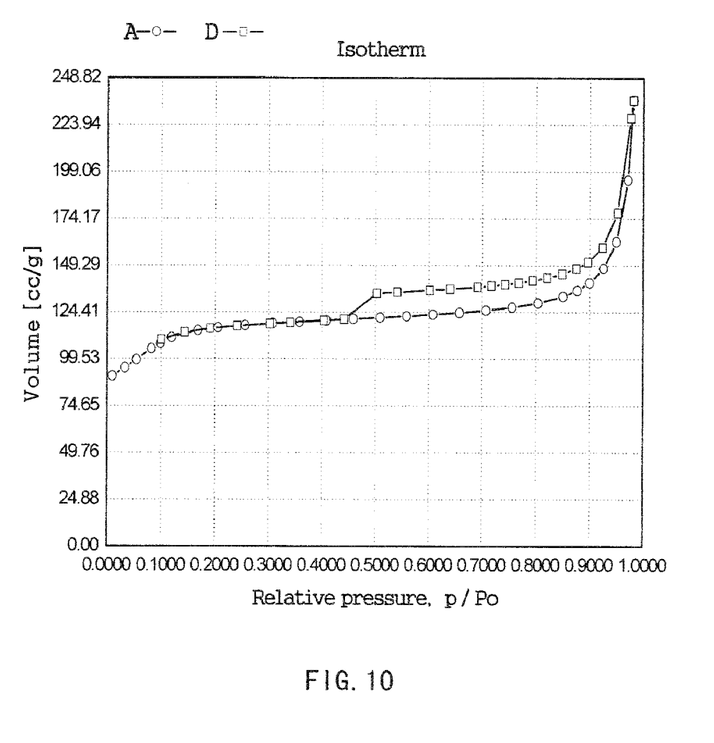
FIG. 10 shows the adsorption-desorption isothermal curve of the low-temperature nitrogen adsorption of Sample I in Example 9.
Figure 22:
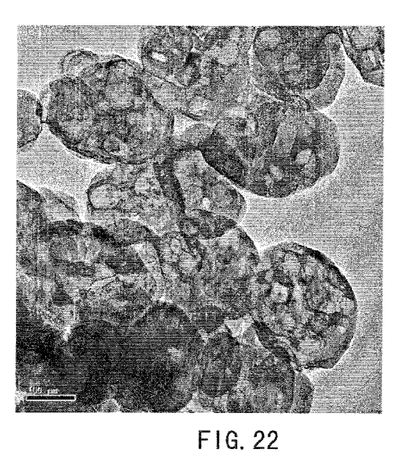
FIG. 22 shows the Transmission Electron Microscope (TEM) photograph of Sample I in Example 9.

20 g of the titanosilicate Ti-ZSM-12, 10 ml of an ethanol solution of palladium acetate having a concentration of 0.01 g/ml (calculated with palladium atom), a suitable amount of sodium citrate and polyethylene glycol were added to an aqueous solution of triethanolamine (having a mass percent concentration of 18%), homogeneously mixed and stirred to obtain a mixture having a titanosilicate (g):polyethylene glycol (molar):triethanolamine (molar):sodium citrate (molar):palladium acetate (g, calculated with palladium):water (molar) ratio of 100:0.01:1.2:0.05:1.0:1500. The mixture was then fed into the reaction kettle, hydrothermally treated for 320 h at 130° C. and an autogenous pressure. The resulted substance was filtered, washed with water, naturally dried and further dried for 3 h at 140° C. to obtain the novel noble metal-containing titanosilicate material I of the present invention. Upon characterization, the material was represented with the oxide form of $0.5TiO_2.100SiO_2.0.7PdO.1.3Pd$. There was a hysteresis loop in the adsorption-desorption isothermal curve of the low-temperature nitrogen adsorption (FIG. 10). The Transmission Electron Microscope (TEM) photograph showed a hollow structure (FIG. 22).

EXAMPLE 10

Figure 11:
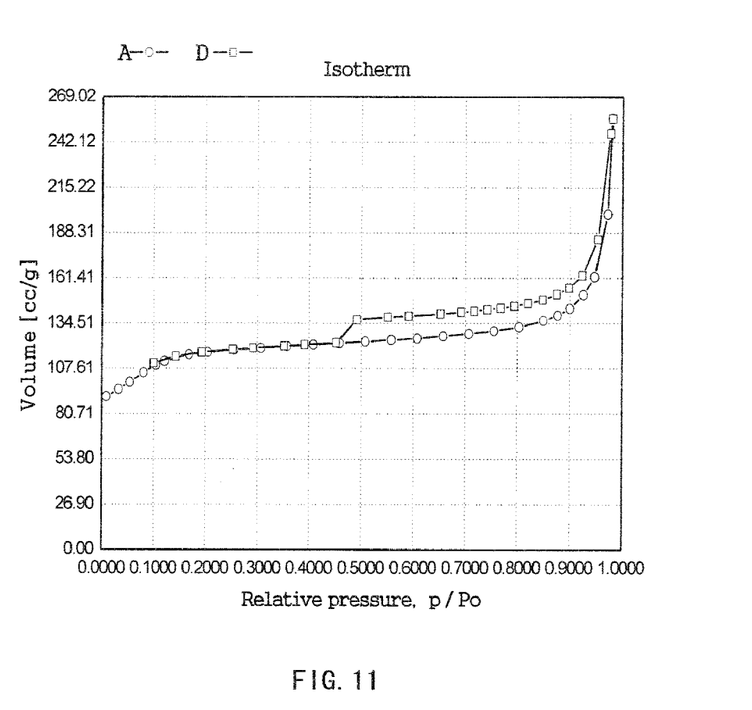
FIG. 11 shows the adsorption-desorption isothermal curve of the low-temperature nitrogen adsorption of Sample J in Example 10.
Figure 23:
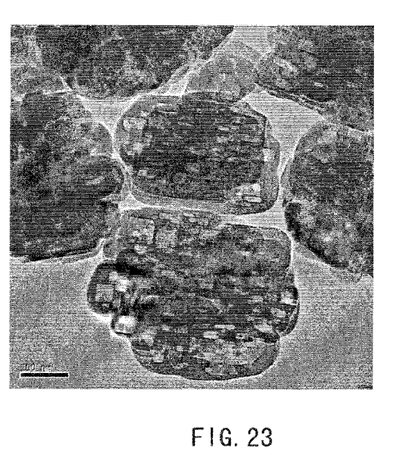
FIG. 23 shows the Transmission Electron Microscope (TEM) photograph of Sample J in Example 10.

Tetraethyl orthosilicate, tetrapropyl titanate, palladium acetate having a concentration of 0.01 g/ml (calculated with palladium atom) and tetradecyl trimethyl ammonium bromide were added to an aqueous solution of tetrapropyl ammonium hydroxide (having a mass percent concentration of 13%), homogeneously mixed and stirred to obtain a mixture having a silicon source:titanium source:alkali source:palladium source:protecting agent:water ratio of 100:0.1:0.1:1.1:0.001:1500, wherein the silicon source is calculated with $SiO_2$ the titanium source is calculated with $TiO_2$; the palladium source is calculated with Pd. The mixture was then fed into the stainless steel sealed reaction kettle, hydrothermally treated for 72 h at 160° C. and an autogenous pressure. The resulted substance was taken out, filtered, dried, and calcined to obtain the intermediate crystalline material. Said intermediate crystalline material was fed into the remnant filtrate, and then a suitable amount of hydrazine hydrochloride was then added for hydrothermal treatment for 36 h at 170° C. and an autogenous pressure. The resulted substance was filtered, washed with water, naturally dried and further dried for 3 h at 150° C. to obtain the novel noble metal-containing titanosilicate material J of the present invention. Upon characterization, the material was represented with the oxide form of $2TiO_2.100SiO_2.0.6PdO.3.3Pd$. There was a hysteresis loop in the adsorption-desorption isothermal curve of the low-temperature nitrogen adsorption (FIG. 11). The Transmission Electron Microscope (TEM) photograph showed a hollow structure (FIG. 23).

EXAMPLE 11

Figure 12:
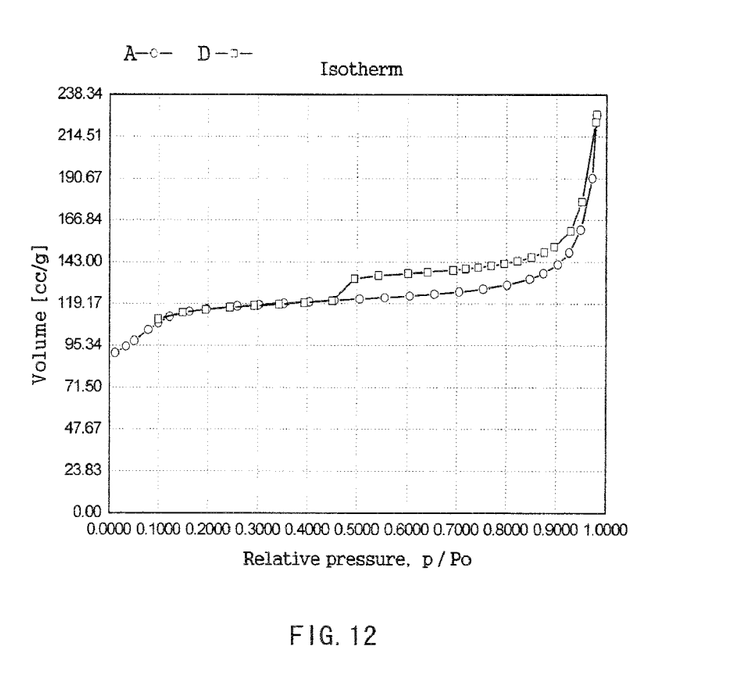
FIG. 12 shows the adsorption-desorption isothermal curve of the low-temperature nitrogen adsorption of Sample K in Example 11.
Figure 24:
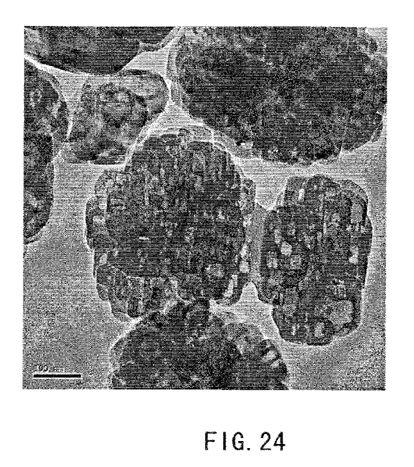
FIG. 24 shows the Transmission Electron Microscope (TEM) photograph of Sample K in Example 11.

20 g of the titanosilicate TS-1, palladium ammonium nitrate and platinum ammonium nitrate complex solution having a concentration of 0.01 g/ml (calculated with palladium or platinum atom), hydrazine hydrate and cetyl trimethyl ammonium bromide were added to an aqueous solution of tetrapropyl ammonium hydroxide (having a mass percent concentration of 14%), homogeneously mixed and stirred to obtain a mixture having a titanosilicate (g):cetyl trimethyl ammonium bromide (molar):tetrapropyl ammonium hydroxide (molar):hydrazine hydrate (molar):platinum ammonium nitrate (g, calculated with platinum):palladium ammonium nitrate (g, calculated with palladium):water (molar) ratio of 100:0.1:1.2:2.0:0.8:1.2:1800. The mixture was then fed into the stainless steel sealed reaction kettle, hydrothermally treated for 72 h at 180° C. and an autogenous pressure. The resulted substance was filtered, washed with water, naturally dried and further dried for 3 h at 180° C. to obtain the novel double noble metal-containing titanosilicate material K of the present invention. Upon characterization, the material was represented with the oxide form of $4TiO_2.100SiO_2.0.3PdO.0.1PtO.0.9Pd.0.7Pt$. There was a hysteresis loop in the adsorption-desorption isothermal curve of the low-temperature nitrogen adsorption (FIG. 12). The Transmission Electron Microscope (TEM) photograph showed a hollow structure (FIG. 24).

COMPARATIVE EXAMPLE 2

This comparative example shows the process of the conventional preparation of the supported-type palladium-platinum/titanosilicate catalyst.

20 g of the titanosilicate TS-1 and each of 10 ml palladium ammonium nitrate and platinum ammonium nitrate complex solutions having a concentration of 0.01 g/ml (calculated with palladium or platinum atom) were added to 20 ml of deionized water. The mixture was homogeneously stirred, properly sealed, impregnated for 24 h at a temperature of 40° C., naturally dried and reduction-activated for 3 h in a hydrogen atmosphere at 150° C. to obtain the conventional supported-type palladium-platinum/titanosilicate catalyst DB-2. Upon characterization, the catalyst was represented with the oxide form of $6TiO_2.100SiO_2.0.8PdO.0.4PtO.0.2Pd.0.5Pt$. There was no hysteresis loop in the adsorption-desorption isothermal curve of the low-temperature nitrogen adsorption. The Transmission Electron Microscope (TEM) photograph showed no hollow structure.

COMPARATIVE EXAMPLE 3

This comparative example shows the process of the conventional preparation of the supported-type palladium/titanosilicate catalyst.

20 g of the titanosilicate prepared according to the method as described in Example 1 of CN1132699C and 20 ml palladium ammonium nitrate complex solution having a concentration of 0.01 g/ml (calculated with palladium atom) were added to 20 ml of deionized water. The mixture was homogeneously stirred, properly sealed, impregnated for 24 h at a temperature of 40° C., naturally dried and reduction-activated for 3 h in a hydrogen atmosphere at 150° C. to obtain the supported-type palladium-platinum/titanosilicate catalyst DB-3. Upon characterization, the catalyst was represented with the oxide form of $6TiO_2.100SiO_2.0.9PdO.0.1Pd$. There was a hysteresis loop in the adsorption-desorption isothermal curve of the low-temperature nitrogen adsorption. The Transmission Electron Microscope (TEM) photograph showed a hollow structure.

COMPARATIVE EXAMPLE 4

This comparative example shows the process of the conventional preparation of the supported-type palladium/titanosilicate catalyst.

20 g of the titanosilicate TS-2 and 15 ml palladium ammonium nitrate complex solution having a concentration of 0.01 g/ml (calculated with palladium atom) were added to 30 ml of deionized water. The mixture was homogeneously stirred, properly sealed, impregnated for 24 h at a temperature of 40° C., naturally dried and reduction-activated for 1 h in a hydrogen atmosphere at 150° C. to obtain the conventional supported-type palladium/titanosilicate catalyst DB-4. Upon characterization, the catalyst was represented with the oxide form of $7TiO_2 \cdot 100SiO_2 \cdot 0.2PdO \cdot 0.6Pd$. There was no hysteresis loop in the adsorption-desorption isothermal curve of the low-temperature nitrogen adsorption. The Transmission Electron Microscope (TEM) photograph showed a solid structure, rather than a hollow structure.

EXAMPLE 12

This Example shows the reaction effects of the preparation of propylene oxide by the propylene gas phase epoxidation of the example samples and the samples prepared in the comparative examples in the present invention in the presence of hydrogen.

0.5 g of each of the samples prepared in Examples 1-11 and Comparative Examples 1, 2, 3 and 4 above was respectively added to the epoxidation reaction vessel containing 80 ml of methanol. Propylene, oxygen, hydrogen and nitrogen were fed into the vessel to form a propylene-oxygen-hydrogen-nitrogen gas mixture (with a molar ratio of 1:1:1:7). The epoxidation of the mixture was carried out under the conditions of 60° C., a pressure of 1.0 MPa and a propylene space velocity of 10 h$^{-1}$ to obtain propylene oxide (PO).

The data of propylene conversion rate and PO selectivity after 2 h and 12 h of the reaction are respectively shown in Tables 1 and 2.

TABLE 1

| Sample Source | Sample No. | Propylene conversion rate % | PO Selectivity % |
|---|---|---|---|
| Example 1 | A | 5.24 | 91.68 |
| Example 2 | B | 5.53 | 92.56 |
| Example 3 | C | 4.36 | 92.14 |
| Example 4 | D | 4.73 | 91.87 |
| Example 5 | E | 4.21 | 91.65 |
| Example 6 | F | 5.21 | 91.45 |
| Example 7 | G | 5.13 | 92.26 |
| Example 8 | H | 4.86 | 92.61 |
| Example 9 | I | 5.32 | 91.29 |
| Example 10 | J | 4.53 | 91.88 |
| Com. Ex. 1 | DB-1 | 2.63 | 89.01 |
| Example 11 | K | 5.45 | 92.14 |
| Com. Ex. 2 | DB-2 | 2.71 | 88.52 |
| Com. Ex. 3 | DB-3 | 2.68 | 89.34 |
| Com. Ex. 4 | DB-4 | 1.14 | 86.65 |

TABLE 2

| Sample Source | Sample No. | Propylene conversion rate % | PO Selectivity % |
|---|---|---|---|
| Example 1 | A | 5.18 | 91.21 |
| Example 2 | B | 5.42 | 92.11 |
| Example 3 | C | 4.35 | 92.06 |
| Example 4 | D | 4.71 | 91.52 |
| Example 5 | E | 4.25 | 91.49 |
| Example 6 | F | 5.20 | 91.43 |
| Example 7 | G | 5.12 | 92.12 |
| Example 8 | H | 4.88 | 92.54 |
| Example 9 | I | 5.14 | 91.07 |
| Example 10 | J | 4.51 | 91.72 |
| Com. Ex. 1 | DB-1 | 0.49 | 80.32 |
| Example 11 | K | 5.42 | 92.03 |
| Com. Ex. 2 | DB-2 | 1.26 | 81.24 |
| Com. Ex. 3 | DB-3 | 1.04 | 82.31 |
| Com. Ex. 4 | DB-4 | 0.61 | 80.28 |

From Tables 1 and 2, it can be seen that the activity of the materials provided in the present invention is obviously higher than those of the comparative samples, and the selectivity thereof is also somewhat increased, which show that the catalytic oxidation activity and selectivity thereof are apparently enhanced over the prior art, and meanwhile, the materials of the present application have better catalytic activity stability.

The data of the benzene adsorption amount under the conditions of 25° C., P/P$_0$=0.10, the adsorption time of 1 h, and the cavity radial length of the samples are shown in Table 3.

TABLE 3

| Sample Source | Sample No. | Benzene adsorption amount, mg/g | Radial length, nm |
|---|---|---|---|
| Example 1 | A | 65 | 10-120 |
| Example 2 | B | 48 | 5-80 |
| Example 3 | C | 56 | 8-90 |
| Example 4 | D | 43 | 5-155 |
| Example 5 | E | 51 | 2-75 |
| Example 6 | F | 71 | 2-200 |
| Example 7 | G | 55 | 5-115 |
| Example 8 | H | 49 | 5-280 |
| Example 9 | I | 44 | 20-180 |
| Example 10 | J | 36 | 0.5-130 |
| Com. Ex. 1 | DB-1 | 22 | — |
| Example 11 | K | 45 | 5-90 |
| Com. Ex. 2 | DB-2 | 19 | — |
| Com. Ex. 3 | DB-3 | 34 | 60-80 |
| Com. Ex. 4 | DB-4 | 28 | — |

What is claimed is:

1. A noble metal-containing titanosilicate material, wherein said material is represented by xTiO$_2$·100SiO$_2$·yEO$_m$·zE in oxide form, wherein x ranges from 0.001 to 50.0; (y+z) ranges from 0.0001 to 20.0 and y/z is greater than zero and <5; E represents one or more noble metals selected from the group consisting of Ru, Rh, Pd, Re, Os, Ir, Pt, Ag and Au; m is a number satisfying the oxidation state of E; and the crystal grains of said material fully or partially contain hollow structures, the titanosilicate material wherein there is a hysteresis loop between an adsorption isotherm measured from said material and a desorption isotherm of a low-temperature nitrogen adsorption measured from said material.

2. The titanosilicate material according to claim 1, wherein said noble metal E is one or more noble metals selected from the group consisting of Pd, Pt, Ag and Au.

3. The titanosilicate material according to claim 2, wherein said noble metal E is Pd and/or Pt.

4. The titanosilicate material according to claim 3, wherein said noble metal E is Pd.

5. The titanosilicate material according to claim 1, wherein x ranges from 0.005 to 25.0; (y+z) ranges from 0.005 to 20.0 and y/z<3.

6. The titanosilicate material according to claim 1, wherein x ranges from 0.001 to 20.0; (y+z) ranges from 0.001 to 10.0 and y/z<2.

7. The titanosilicate material according to claim 1, wherein x ranges from 0.005 to 20.0; and (y+z) ranges from 0.005 to 10.0 and y/z<1.

8. The titanosilicate material according to claim 1, wherein the benzene adsorption capacity of said material is at least 25 mg/g, measured under the conditions of a temperature of 25° C., $P/P_0$=0.10 and the adsorption time of 1 h.

9. The titanosilicate material according to claim 1, wherein the benzene adsorption capacity of said material is at least 35 mg/g, measured under the conditions of a temperature of 25° C., $P/P_0$=0.10 and the adsorption time of 1 h.

10. The titanosilicate material according to claim 1, wherein at a relative pressure $P/P_0$ of about 0.60, the difference between a nitrogen adsorption capacity during a desorption measured from said material and a nitrogen adsorption capacity during an adsorption measured from said material is greater than 2% of the nitrogen adsorption capacity during the adsorption measured from said material.

11. The titanosilicate material according to claim 1, wherein the cavity portions of the hollow crystal grains of said material have radial length of 0.1-500 nm.

12. The titanosilicate material according to claim 1, wherein the cavity portions of the hollow crystal grains of said material have radial length of 0.5-300 nm.

13. The titanosilicate material according to claim 1, wherein the cavity portions of the hollow crystal grains of said material has have shapes selected from rectangle, circularity, irregular circularity, irregular polygon, and combinations thereof.

14. The titanosilicate material according to claim 1, wherein the crystal grains of said material are single crystal grains.

15. The titanosilicate material according to claim 1, wherein the crystal grains of said material are aggregate crystal grains aggregated from a plurality of crystal grains.

16. The titanosilicate material according to claim 1, wherein y/z is 0.0016 to <5.

17. A method for preparing a noble metal-containing titanosilicate material according to claim 1, characterized in comprising the following steps:
   (1) homogeneously mixing titanium source, silicon source, alkali source, protecting agent, noble metal source with water to obtain a mixture having a silicon source:titanium source:alkali source:noble metal source:protecting agent:water ratio of 100:(0.005-50.0):(0.005-20.0):(0.005-10.0):(0.0001-5.0):(200-10000), wherein the silicon source is calculated with $SiO_2$; the titanium source is calculated with $TiO_2$; and the noble metal source is calculated with simple substance; hydrothermally crystallizing the mixture for at least 2 h at 120-200° C., taking out, filtering, drying and calcining the product to obtain an intermediate crystalline material;
   (2) feeding the intermediate crystalline material obtained in step (1) into the filtrate obtained after filtration in step (1), adding a reducing agent in a molar ratio of 0.1-10 to the noble metal source added in step (1), hydrothermally treating for 2-360 h at 80-200° C. and an autogenous pressure, and recovering the product to obtain a titanosilicate material.

18. The preparation method according to claim 17, characterizing in that the silicon source in step (1) is selected from the group consisting of silica gel, silica sol and organic silicate.

19. The preparation method according to claim 18, characterizing in that the organic silicate has the general formula $R^4_4SiO_4$, wherein $R^1$ is alkyl having 1-4 carbon atoms.

20. The preparation method according to claim 19, characterizing in that $R^4$ is ethyl.

21. The preparation method according to claim 17, characterizing in that the titanium source is an inorganic titanium salt or an organic titanate.

22. The preparation method according to claim 21, characterizing in that the inorganic titanium salt is selected from the group consisting of $TiCl_4$, $Ti(SO_4)_2$ and $TiOCl_2$.

23. The preparation method according to claim 21, characterizing in that the organic titanate has the general formula of $Ti(OR^5)_4$, wherein $R^5$ is alkyl having 1-6 carbon atoms.

24. The preparation method according to claim 23, characterizing in that $R^5$ is alkyl having 2-4 carbon atoms.

25. The preparation method according to claim 17, characterizing in that the alkali source in step (1) is a quaternary ammonium alkali compound or a mixture of a quaternary ammonium alkali compound, an aliphatic amine compound and an alcohol amine compound.

26. The preparation method according to claim 25, characterizing in that the quaternary ammonium alkali compound has the general formula of $(R^6)_4NOH$, wherein $R^6$ is alkyl having 1-4 carbon atoms.

27. The preparation method according to claim 26, characterizing in that $R^6$ is propyl.

28. The preparation method according to claim 25, characterizing in that the aliphatic amine compound has the general formula of $R^7(NH_2)_n$, wherein $R^7$ is alkyl or alkylidene having 1-6 carbon atoms, and n is 1 or 2.

29. The preparation method according to claim 25, characterizing in that the aliphatic amine compound is selected from the group consisting of ethylamine, n-butylamine, butanediamine and hexanediamine.

30. The preparation method according to claim 25, characterizing in that the alcohol amine compound has the general formula of $(HOR^8)_m NH_{(3-m)}$, wherein $R^8$ is alkyl having 1-4 carbon atoms, and m is 1, 2 or 3.

31. The preparation method according to claim 25, characterizing in that the alcohol amine compound is selected from the group consisting of monoethanolamine, diethanolamine and triethanolamine.

32. The preparation method according to claim 17, characterizing in that the protecting agent in step (1) is a polymer or surfactant, wherein said polymer is selected from the group consisting of polypropylene, polyethyleneglycol, polystyrene, polyvinyl chloride, polyethylene and derivatives thereof, and mixtures thereof; and the surfactant is selected from the group consisting of anionic surfactant, cationic surfactant and nonionic surfactant.

33. The preparation method according to claim 17, characterizing in that the noble metal source in step (1) is an inorganic or organic substance of said noble metal.

34. The preparation method according to claim 33, characterizing in that the noble metal source is an inorganic or organic palladium source.

35. The preparation method according to claim 34, characterizing in that the inorganic palladium source is selected from the group consisting of palladium oxide, palladium carbonate, palladium chloride, palladium nitrate, palladium ammonium nitrate, palladium sal ammoniac, palladium hydroxide and other complexes of palladium; and said organic palladium source is selected from the group consisting of palladium acetate and palladium acetylacetone.

36. The preparation method according to claim 17, characterizing in that the mixture in step (1) has a silicon source:titanium source:alkali source:palladium source:protecting agent:water molar ratio of 100:(0.01-10.0):(0.01-10.0):(0.01-5.0):(0.0005-1.0):(500-5000).

37. The preparation method according to claim 17, characterizing in that the reducing agent in step (2) is selected from the group consisting of hydroxylamine, hydrazine, borohydride, sodium citrate, and mixtures thereof.

38. The preparation method according to claim 37, characterizing in that the hydrazine is selected from the group consisting of hydrazine hydrate, hydrazine hydrochloride and hydrazine sulphate; and said borohydride is selected from the group consisting of sodium borohydride and potassium borohydride.

* * * * *